(12) United States Patent
Sadowski et al.

(10) Patent No.: US 9,977,862 B2
(45) Date of Patent: May 22, 2018

(54) BIOPROCESS METHOD AND SYSTEM

(71) Applicant: SYNTHACE LIMITED, London (GB)

(72) Inventors: Michael Ian Sadowski, London (GB); Sean Michael Ward, London (GB)

(73) Assignee: SYNTHACE LIMITED, London (GB)

( * ) Notice: Subject to any disclaimer, the term of this patent is extended or adjusted under 35 U.S.C. 154(b) by 0 days. days.

(21) Appl. No.: 15/271,592

(22) Filed: Sep. 21, 2016

(65) Prior Publication Data

US 2017/0011170 A1 Jan. 12, 2017

Related U.S. Application Data

(63) Continuation of application No. PCT/US2015/022280, filed on Mar. 24, 2015.

(30) Foreign Application Priority Data

Mar. 24, 2014 (GB) .................................. 1405246.8

(51) Int. Cl.
*G01N 33/48* (2006.01)
*G06F 19/28* (2011.01)
*G06G 7/58* (2006.01)

(52) U.S. Cl.
CPC .................................. *G06F 19/28* (2013.01)

(58) Field of Classification Search
CPC .......... G06F 19/18; G06F 19/20; G06F 19/22; G06F 19/28; G06F 19/32; G06F 19/3223
See application file for complete search history.

(56) References Cited

U.S. PATENT DOCUMENTS 6,311,095 B1 10/2001 Brown
2013/0260419 A1 10/2013 Ransohoff et al.

OTHER PUBLICATIONS

International Search Report and Written Opinion dated May 26, 2015 in PCT/US2015/022280.
Fisher et al., "Executable cell biology," Nature Biotechnology, vol. 25, No. 11, pp. 1239-1249 (2007).
Lee et al., "Monitoring of a sequencing batch reactor using adaptive multiblock principal component analysis," Biotechnology and Bioengineering, vol. 82, No. 4, pp. 489-497 (2003).
Website: http://antha-lang.org/ (Nov. 17, 2014, tracked by Wayback machine).
European Search Report dated Oct. 17, 2017 in European Application No. EP 15770137.
Cieślik, et al., "A lightweight, flow-based toolkit for parallel and distributed bioinformatics pipelines", BMC Bioinformatics, vol. 12, No. 1, Feb. 25, 2011, 11 pages.

*Primary Examiner* — Eric S Dejong
(74) *Attorney, Agent, or Firm* — Perkins Coie LLP; Viola T. Kung

(57) ABSTRACT

Methods, systems and apparatus for performing a biological process are provided, wherein the method comprises implementation of at least one unit operation, and wherein the unit operation is defined according to a standardised element structure, the element structure comprising a plurality of functional section blocks, and wherein the section blocks comprise at least one of the group consisting of: imports; parameters; data; physical inputs; requirements; setup; and execution steps.

13 Claims, 4 Drawing Sheets

Figure 3

Figure 1:
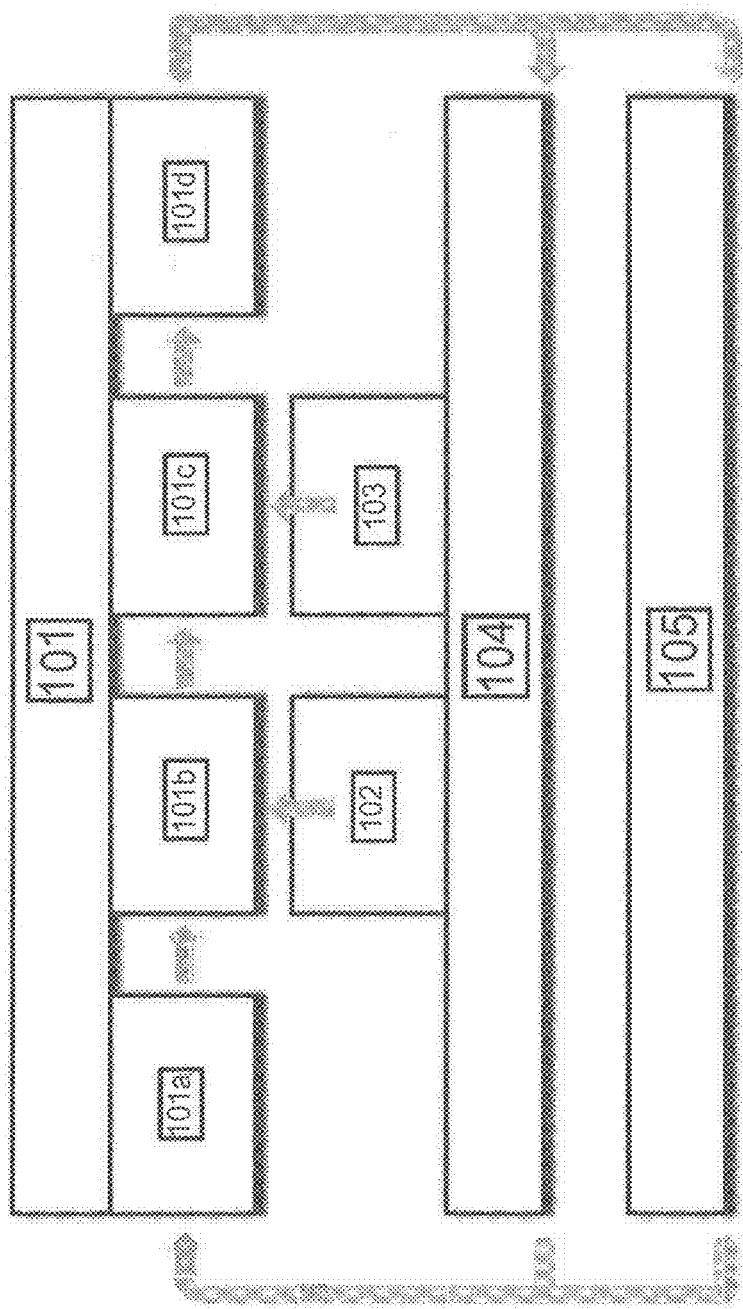

```
1  // Example syntax
2  protocol bradford //import "github.com/antha-lang/antha/examples/bradford"
3  import (
4      "plateReader"
5  )
6  Parameters (
7      SampleVolume Volume = 15.(uL)
8  )
9  Data (
10 )
11 Inputs (
12 )
13 Outputs (
14 )
15 Requirements (
16 )
17 Setup (
18 )
19 Steps (
20 )
21 Analysis (
22 )
23 Validation (
24 )
```

BIOPROCESS METHOD AND SYSTEM

This application is a continuation of PCT/US2015/022280, filed Mar. 24, 2015, which claims priority of GB1405246.8, filed Mar. 24, 2014. The contents of the above identified applications are incorporated herein by reference in their entirety.

FIELD OF THE INVENTION

Methods and systems for design and execution of experiments are considered in this invention, in particular design and implementation of bioprocess manufacturing via automated laboratory systems.

BACKGROUND OF THE INVENTION

When assembling a biological synthetic process, multiple alternatives typically exist for each of the operations and parts in the process, such as the structure and identity of the genetic constructs used, the particular protocol used to perform a step such as a transformation, purification etc. The question of how to design the most efficient process is therefore one of choosing a set of parts and operations, in order to satisfy design criteria such as maximising yield of the required output.

There are very large numbers of variables that influence the overall yield of product in a biological synthetic process, such as the host organism selected and the particular strain of host species used, physical factors such as temperature, pH and oxygen availability and timing of reactions, to name a few. Therefore, the choice of suitable parts and operations that make up a multi-step process has to be made in the context of a highly dimensional design space. Often the combination of variables that work in the context of one manufacturing facility cannot be easily transposed to other facilities. This leads to considerable difficulties in standardisation of bio-processing and represents a key challenge for the future of synthetic biology. By way of example, a 2012 report in Nature recounted that scientists at biotech company Amgen had only managed to reproduce around 11% of 53 published cancer-related studies which they had attempted over the previous years (Begley C. G & Ellis L. M., Nature 483, 531-533 (29 Mar. 2012). Similarly, the pharmaceutical company Bayer has indicated that in their estimation only 20-25% of published data corresponded to their own in-house findings (Prinz, F., Schlange, T. & Asadullah, K. Nature Rev. Drug Discov. 10, 712 (2011)).

Conventionally, essential process or experimental design decisions have to-date been made arbitrarily based on what is usual in the art, available or known to the experimenter or manufacturer at the time of setting up the process or experimental pipeline. Decisions in biological process design are often habitual or based upon artisanal know-how passed down within laboratories or industrial organisations. This is often complicated with time and resource constraints leading to a trial and error development in which a pipeline is adjusted by exchanging discrete parts and operations or modifying parameters, in order to improve the features of the starting pipeline. This results in design decisions that are often suboptimal or require substantial resources to identify reagents, operations and parameters that might be merely satisfactory. Hence, there can be considerable institutional resistance to change a process once it has been settled upon due to the inherent uncertainty associated with the optimization strategy as a whole.

Despite these problems many successful bioprocesses have been developed and there is a recognised potential for bio-based manufacturing to provide enormous benefits across many areas. Hence, there exists a need in the art—particularly within synthetic biology—to provide methods and systems that can facilitate the design of experimental or production pipelines from the level of the laboratory bench up to and including the industrial-scale bioreactor. In particular there is a need to provide methods and systems that can facilitate like-for-like comparisons between processes as well as standardised approaches for defining parts and protocols that may be used in experimental design, bioprocessing and manufacturing. To achieve this, there exists a need in the art to provide methods and systems that can facilitate reliable design of experiments from the level of the lab bench up to and including the industrial-scale bioreactor. These and other uses, features and advantages of the invention should be apparent to those skilled in the art from the teachings provided herein.

SUMMARY OF THE INVENTION

The present inventors have overcome the problems associated with the art by providing methods and systems for reproducible and scalable bioprocess workflows via stacking of smart and reusable elements.

Accordingly a first aspect of the invention provides a method for performing a biological process wherein the method comprises implementation of at least one unit operation, and wherein the unit operation is defined according to a standardised element structure, the element structure comprising a plurality of functional section blocks, and wherein the section blocks comprise at least one of the group consisting of: imports; parameters; data; physical inputs; requirements; setup; and execution steps. Suitably, the element structure further comprises at least one additional section block selected from the group consisting of: physical outputs, analysis and validation steps. Optionally, the element structure comprises at least the sections blocks defining: imports; parameters; data; physical inputs; requirements; setup; and execution steps.

In a specific embodiment of the invention the biological process comprises at least two unit operations, wherein each unit operation defined according to a standardised element structure. Suitably a plurality of unit operations may be arranged in sequence or in parallel to create a workflow. In a further embodiment of the invention the least two unit operations are non-identical.

In yet a further embodiment of the invention, the unit operation is selected from the group consisting of: a conversion; a reaction; a purification; a construct assembly step; an assay or analysis such as a quantification of a product, a by-product or reagent; a nucleotide or protein/peptide synthesis; a cell culture; an incubation; a restriction; a ligation; a mutation; an inoculation; a lysis; a transformation; an extraction; the conditioning of a product (e.g. for storage); and an amplification (e.g. with respect to a nucleic acid). Optionally, the biological process is either a manufacturing process and/or an analytical process. Suitably the process may comprise at least two unit operations, at least one of which is a process operation and at least one of which is an analytical process operation.

A second aspect of the invention provides a computer implemented method comprising any of the method steps described herein.

A third aspect of the invention provides a system for performing a biological process, comprising:

a server with processing modules adapted to implement the methods as described herein;

a data storing means which is accessible by the processor for maintaining a record of standardised elements, wherein each standardised element defines a unit operation in a biological process; and an interface for accessing the method.

Suitably, the data storing means is a database and/or the data is provided through a cloud service. Optionally, the system comprises a website or a mobile device or computer application to access the service. Typically, the system may be incorporated as part of a laboratory information management system (LIMS).

A fourth aspect of the invention provides a computer readable medium comprising a database, wherein the database comprises a plurality of unit operations, each unit operation being suitable for use within a biological process and wherein each unit operation is defined according to a standardised element structure, the element structure comprising a plurality of functional section blocks, and wherein the section blocks comprise at least one of the group consisting of: imports; parameters; data; physical inputs; requirements; setup; and execution steps. Typically, the element structure further comprises at least one additional section block selected from the group consisting of: physical outputs, analysis and validation steps. Suitably, the element structure comprises at least the section blocks defining: imports; parameters; data; physical inputs; requirements; setup; and execution steps.

A fifth aspect of the invention provides an apparatus comprising the computer readable medium described herein. In a specific embodiment, the apparatus comprises one or more memories and one or more processors, and wherein the one or more memories and the one or more processors are in electronic communication with each other, the one or more memories tangibly encoding a set of instructions for implementing the methods of the invention as described.

A sixth aspect of the invention provides a computer implemented method for designing an experiment comprising the steps of:
  (i) selecting an input and a desired output for the experiment, wherein the input comprises physical input and the output is selected from either or both of a physical output and an information output; and
  (ii) determining a process for conversion of the input to the desired output, wherein the process comprises at least one unit operation, and wherein the unit operation is selected from a database that comprises a plurality of potential unit operations;
wherein the unit operation is defined according to a standardised element structure, the element structure comprising a plurality of functional section blocks, and wherein the section blocks comprise: imports; parameters; data; physical inputs; requirements; setup; and execution steps.

A seventh aspect of the invention provides an apparatus comprising one or more memories and one or more processors, and wherein the one or more memories and the one or more processors are in electronic communication with each other, the one or more memories tangibly encoding a set of instructions for implementing the methods described herein.

DRAWINGS

Figure 2A:
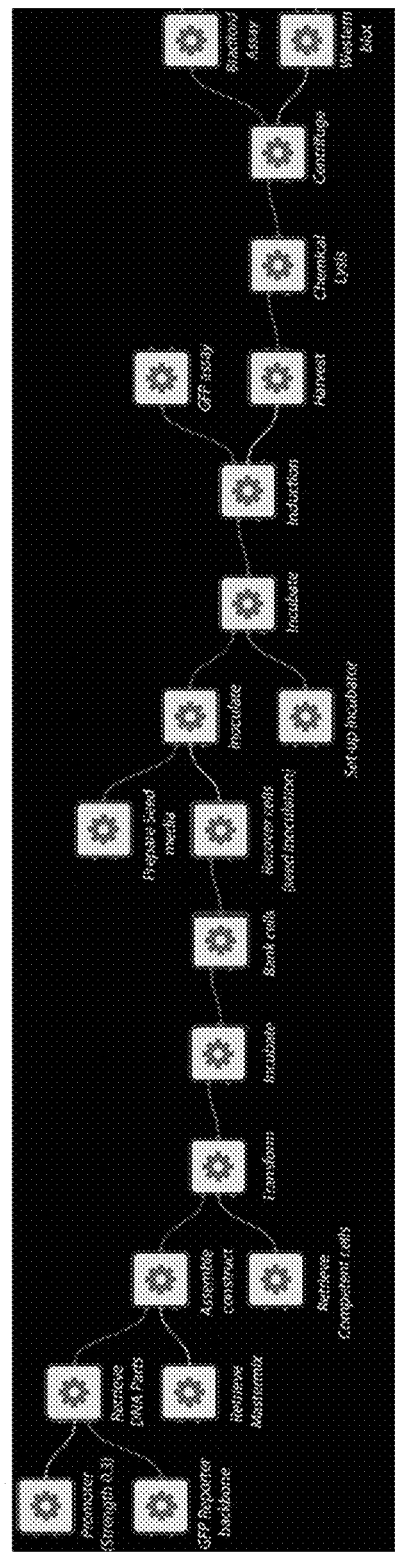
Figure 2B:
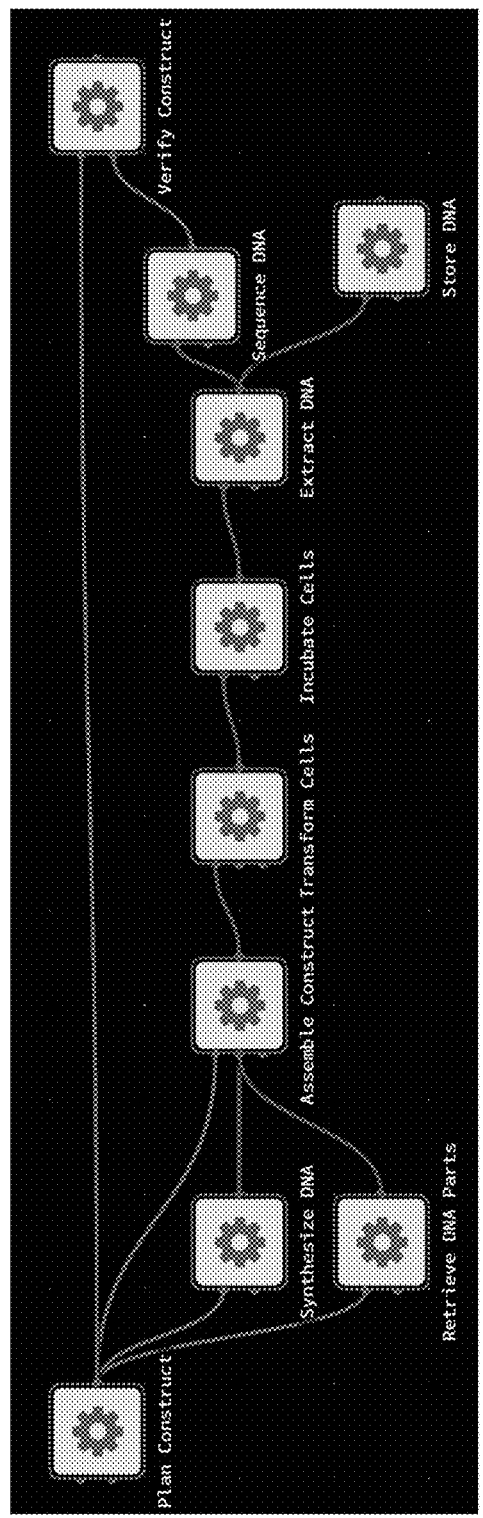

The invention is further illustrated with reference to the following drawings in which FIG. 1 shows a flow diagram according to one embodiment of the present invention FIGS. 2 (a) and (b) show exemplary bioprocess workflows according to embodiments of the present invention, each unit operation is defined by an element shown as a box containing a cog-shaped wheel symbol.

FIG. 3 shows the multi-section structure of an element according to one embodiment of the present invention

DETAILED DESCRIPTION OF THE INVENTION

All references cited herein are incorporated by reference in their entirety. Unless otherwise defined, all technical and scientific terms used herein have the same meaning as commonly understood by one of ordinary skill in the art to which this invention belongs.

Prior to setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "process" is defined as a specific sequence of transformative events performed upon a starting material in order to achieve a specified purpose or goal. The process may result in the transformation of the starting material into a product—in which case the process is a "production process". Alternatively, the process may result in the determination of information about the starting material—in which case the process may be diagnostic or prognostic in nature. The overall process may be sub-divided into individual process steps that are applied in sequence to achieve the desired outcome. According to an embodiment of the invention, the process is a "bio-process" that uses complete living cells or their components (e.g., prokaryotic or eukaryotic cells, enzymes, organelles such as chloroplasts) to obtain desired products. The processes of the present invention are subject to process variables that are referred to as factors. Hence, a process comprises a set of steps that are applied on inputs (including at least a physical input) in order to produce an output (including at least a physical output such as a product, and possibly additional data outputs). Inputs may comprise physical starting materials selected from one or more of the group consisting of: reagents; cells; cellular derivatives; cellular extracts; tissue extracts; polypeptides; peptides; proteins; nucleic acids; small molecules; oligosaccharides; polysaccharides; polymeric molecules; elements; organic or inorganic salts; pharmaceutical compounds; pro-drugs; and any other composition of matter suitable for use within a biological process. An embodiment of the invention may include a process which involves the introduction of one or more genes into a microorganism, which in turn expresses one or more proteins encoded by those genes or modifies the metabolic processes of the organism by the expression of non-protein-coding genes or other alterations to the genetic makeup of the host. The protein(s) itself is may be the desired product or where it functions as part of a pathway, the protein may contribute to the generation of a desired product.

The term "unit operation" is defined as any step or sub-step in a process that can be identified as a self-contained process or "unit" which contributes to a set of successive steps—or units—that together serve to make up a complete process. Suitably, a unit operation may be selected from one or more of: a conversion; a reaction; a purification; a construct assembly step; an assay or analysis such as a quantification of a product, a by-product or reagent; a sequencing of nucleic acids; a physical mixing; a centrifugation; a spreading or physical plating of a sample; the selective sampling of a sub population of a sample, such as colony picking; the three dimensional placement of a sample into a structural matrix; a nucleotide or protein/peptide synthesis; a fermentation; a cell culture; an incubation; a restriction; a ligation; a mutation; a transformation; a specific computation analysis, such as a linear regression, sequence alignment, or model based prediction; a separation such as chromatography; a filtration; a concentration; an evaporation; a desiccation; a wash; an extraction; the conditioning of a product (e.g. for storage); and an amplification (e.g. with respect to a nucleic acid). It will be appreciated that the aforementioned does not represent an exhaustive list of potential unit operations, which are typically reliant upon the precise nature of the process that is to be undertaken.

The term "parts" refers to any physical element utilised within a process or unit operation. Suitably, a part may be a reagent, product, or input to any unit operation, or any piece of equipment or apparatus that is used in a process or unit operation. Typical parts may be selected from one or more of: a variant of a gene or polynucleotide; a genetic construct; a whole cell or cell line; an enzyme; an antibody; a small molecule; a solution (such as buffers, reagents, culture media, etc.); a solid support; a container (such as reaction tanks, flasks, slides, beads or physical interaction substrates, etc.); a peptide; a polypeptide; a functional or non-functional nucleic acid; a nutrient compound; a growth factor; a cytokine; an element; an ionic substance, such as an organic or inorganic anion or cation; and a gas or vapour in the environment of the process. It will be appreciated that the aforementioned does not represent an exhaustive list of potential parts, which are typically reliant upon the precise nature of the process that is to be undertaken.

The term "product" is defined as any desirable physical output of a process. Suitably, a product may include a eukaryotic or prokaryotic organism, virus, nanostructure, a protein, polypeptide, polynucleotide, polymer, tissue, complex or small molecule that is produced as a result of the process. In some processes the product is in fact an information object, such as a digital genetic sequence, or a measurement of system properties that is the result of a destructive or non-destructive assay. It will be appreciated that the aforementioned does not represent an exhaustive list of potential products, which are typically reliant upon the precise nature of the process that is to be undertaken.

The term "protocol" refers to a set of instructions for performing a unit operation. Typically, the set of instructions may be a non-exhaustive list of actions and associated parameters that have to be performed, such that a series of variables are set by the protocol while additional variables are left to the user. Typical variables that are set by a protocol may include the identity and/or concentration of inputs to the operation, the order and/or timing of performing various steps in the protocol, the value of physical parameters which have to be set for some or all steps of the protocol (such as e.g. the temperature, pH, oxygen concentration, mixing speed, etc.), features of the equipment used, and factors such as selecting between alternative calculation models or analysis techniques for computationally derived steps. It will be appreciated that the aforementioned does not represent an exhaustive list of potential elements of a protocol, which are typically reliant upon the precise nature of the process that is to be undertaken.

The term "factor" is used herein to denote any defined feature of or within a process that can be modified without changing the ultimate goal of the process. According to one embodiment of the present invention there are two categories of factors: genetic and process factors.

"Process factors" suitably relate to features of a process which are not associated with the genetics of a construct or host. Typical process factors may include features of the equipment (e.g. dimensions of a reaction tank, impeller configurations, siting of probes), environment (e.g. temperature, pH, oxygenation, atmospheric pressure), protocol (e.g. timings of significant stages and events such as inoculation and induction), reagents (growth media composition, nutrient level, feedstock concentration, inducer concentration), handling of cells (stock storage conditions, size of inoculations between reactors), process design (number of process steps, type of reaction vessel). It will be appreciated that the aforementioned does not represent an exhaustive list of potential process factors, which are typically reliant upon the precise nature of the process that is to be undertaken.

"Genetic factors" suitably relate to qualitative and quantitative features associated with any genetic material involved in a process, for example, such as features of the specific genetic 'construct' which is used to introduce new nucleic acid, including DNA, into the host (e.g. identity or composition of vector), features of the host microorganism (e.g. strain, genetic background (including knockouts of undesirable genes and protein overexpression, epigenetic factors), features of functional DNA (e.g. promoter strength, ribosome binding site strength, plasmid origin of replication, terminator, codon usage strategy, operator, activator, gene variant). It will be appreciated that the aforementioned does not represent an exhaustive list of potential genetic factors, which are typically reliant upon the precise nature of the process that is to be undertaken.

Factors, whether process or genetic factors, are deemed to interact when the effects of changes to one factor are dependent on the value of another factor. Typically, a given process step within a process—such as a bioprocess—may comprise a plurality of factors that can interact with each other. Hence, when one factor is altered as a result of a change in a process parameter, or the inherent characteristics associated with that factor are changed, there can be a cascade of interactions that will modify the effects of other factors within that process step in a causative manner. Where a process comprises more than one process step, this cascade of interactions may lead to additional interactions within factors of neighbouring or even distant process steps. It follows, therefore, that many processes can be considered to be multi-factorial in nature.

The term "score" refers to any interpretable objective or subjective measurement of the suitability of a part, unit operation or protocol for a given purpose within a process. Suitably, a score may be in the form of a user-defined rating (such as e.g. in a range of a minimum to a maximum number of stars, points, etc.), a grade, a proportion of positive evaluations, or a colour (such as a traffic light ranking), or a Boolean indicator (such as a thumbs up or thumbs down symbol). In some embodiments, a score may be in the form of a quantifiable or measurable feature of a part or operation, such as e.g. the quantity, purity, productivity, efficacy of a product output; the quantity of a by-product or contaminant present; the yield of a process; and the cost, energy or time efficiency of a part or unit operation. It will be appreciated that the aforementioned does not represent an exhaustive list of potential scores, which are typically reliant upon the precise nature of the process that is to be undertaken.

The term "context" as used herein refers to the situational information associated with a specified user. Context as applied to a multidimensional rating or score provides a perspective to the value ascribed by a score. It will be appreciated that virtually every user will have a unique perspective when providing a rating for any a given unit operation. The context will depend, in part, upon the parts available to the user, the success of those parts (e.g. apparatus, infrastructure) in performing a unit operation, the success of the unit operation within the process as a whole or in combination with other unit operations (e.g. compatibility with other unit operations) and any factor variables associated with the user.

The term "element" as used herein comprises a standardised description of a part, protocol and/or unit operation that can be utilised within a biological process. In this way, an element represents a reusable unit which can be combined with other elements to form process workflows and pipelines. According to an embodiment of the invention, the elements can robustly describe the inputs and outputs of unit operations. This includes both the information flow and the physical sample flow, with strong typing ensuring compatibility with other unit operations. Typically an element will relate to a single workflow within a given unit operation with a defined set up physical and information inputs being processed into a defined set of physical and information outputs.

In a specific embodiment of the invention, the described method can be implemented via one or more computer systems. In another embodiment the invention provides a computer readable medium containing program instructions for implementing the method of the invention, wherein execution of the program instructions by one or more processors of a computer system causes the one or more processors to carry out the phases as described herein. Suitably, the computer system includes at least: an input device, an output device, a storage medium, and a microprocessor). Possible input devices include a keyboard, a computer mouse, a touch screen, and the like. Output devices computer monitor, a liquid-crystal display (LCD), light emitting diode (LED) computer monitor, virtual reality (VR) headset and the like. In addition, information can be output to a user, a user interface device, a computer-readable storage medium, or another local or networked computer. Storage media include various types of memory such as a hard disk, RAM, flash memory, and other magnetic, optical, physical, or electronic memory devices. The microprocessor is any typical computer microprocessor for performing calculations and directing other functions for performing input, output, calculation, and display of data. Two or more computer systems may be linked using wired or wireless means and may communicate with one another or with other computer systems directly and/or using a publicly-available networking system such as the Internet. Networking of computers permits various aspects of the invention to be carried out, stored in, and shared amongst one or more computer systems locally and at remote sites. In one embodiment of the invention, the computer processor may comprise an artificial neural network (ANN). In a further embodiment of the invention the method may be incorporated as part of a laboratory information management system (LIMS) or a software suite that is compatible with a LIMS.

The methods of the invention may be configured to interact with and control automated laboratory equipment including liquid handling and dispensing apparatus or more advanced laboratory robotic systems. Where higher numbers of factors are considered during the factor screening phase, in one embodiment of the invention it is an option to automate performance of factor screening experiments using a high-level programming language to produce reproducible and scalable workflows to underpin the screening, refining and optimisation phases of the method. Suitable high-level programming languages may include C++, Java™, Visual Basic, Ruby, Google® Go and PHP, as well as the biology specific language Antha™ (www.antha-lang.org).

FIG. 1 is a flow diagram that shows a computer implemented platform for the design of experiments or biological processes by a user that utilises various interacting modules. In one embodiment of the invention the user will access the platform via a user interface (105) so as to access a workflow design tool (101). The user interface (105) may be comprised within a laboratory information management system (LIMS) package, via a dedicated software application (an 'app'), via a website or any other suitable user interface. The workflow design tool (101) enables the user to specify the type of experiment or biological process that is under consideration, especially by specifying inputs (e.g. starting materials) and the desired outputs (e.g. products). In defining the objectives of the experiment or process the workflow design tool (101) the user is able to access the experimental design module (101a) which provides a mechanism for breaking down the experiment or process into one or more unit operations.

Each unit operation will comprise one or more parts and one or more protocols. Selection of the most appropriate components of the one or more unit operation can be accomplished within the parts module (101b) and the protocols module (101c). The parts module (101b) and the protocols module (101c) respectively are able to access a library of compatible standardised parts and protocols comprised within a parts characterisation module (102) and a protocol definition module (103). A fully assembled workflow provides a process pipeline that comprises at least one unit operation, more typically a plurality of unit operations such as the ones shown in FIGS. 2 (a) and (b). The fully assembled workflow can be tested for compatibility with the user's available parts—including laboratory automation apparatus—so as to provide a validation of the workflow within the specific context of the user. Validation can be carried out via the analysis module (101d). It is optional for unit operations to subject to associated scoring or rating criteria that allow for comparison of the user's unique context with the suggested workflow. Hence, the workflow design tool (101) provides capability to establish a design space in part defined by the user's unique context and, in so doing, only permits assembly of a workflow that is compatible with the user contextualised design space.

One important aspect of the platform is that it permits certain degrees of freedom for users to modify unit operations in order to improve compatibility with available parts and associated protocols. This advantageously enables a level of flexibility within the design space as well as an evolution of unit operations to accommodate slightly different user contexts. Once a validated process pipeline is approved by the user the workflow can be implemented either via fully automated laboratory systems or via a manual implementation, or a combination of both. As the unit operations within the pipeline are completed the laboratory automation apparatus and/or the user are prompted to provide feedback metrics on the successful performance of the unit operation as well as the assembled pipeline as a whole. Feedback metrics may include, for example, scores, ratings, data and information on reaction conditions, yield of product, time taken for completion of the protocol, purity of the product, amongst others. The feedback metrics may be combined together with the information regarding the process pipeline and communicated to a standardisation engine (104).

The standardisation engine (104) provides a function of data standardisation, including normalisation, reformatting and parsing on the input information that includes the pipeline process assembly and any accompanying modifications made by the user, together with associated metrics and scores. Data standardisation may comprise removal of extraneous or irrelevant information as well as normalisation of data or values to common or standard form, such as via reference to lookup tables. In so doing, the standardisation engine (104) transforms the input data into a common representation of values thereby providing a consistent record. The standardisation engine (104) may comprise a database of standardised unit operations, parts and protocols. Optionally the standardisation engine (104) does not comprise a database itself but communicates with a database within a separate module (not shown), or within one or more databases comprised within the workflow design tool (101). The standardisation engine provides standardised descriptions of parts to the parts characterisation module (102) and the protocol definition module (103) respectively. Hence, the computer implemented platform provides an iterative procedure for assembling unit operations from standardised parts and procedures that are continually improved, adapted and modified dependent upon the user's context. Suitably, the unit operations are defined in a standardised element structure, described further below. Where the platform is accessed by multiple users, such as in the instance of a multi-user cloud or internet based platform, users will benefit from the continual generation of novel and/or improved parts, protocols and associated unit operations.

In accordance with one embodiment of the invention, the workflow design tool (101) may select one or more unit operations that are defined as elements. Hence, as in FIGS. 2 (*a*) and (*b*), each unit operation in the finally assembled workflow consists of an element.

A specific embodiment of the invention provides a method for performing or designing a biological process—including one or more experimental steps—wherein the method is comprised of at least one unit operation, and wherein the unit operation is defined according to standardised element structure. The element according to this embodiment is shown in FIG. 3 as having a section-based format that defines information as well as the physical inputs and outputs of the unit operation. The use of a structured, text-based format with a domain specific vocabulary also permits the use of version control systems to track how protocols evolve and change over time and to identify which changes are responsible for particular behaviour, also avoiding repetition of errors. In one embodiment of the invention the elements are configured to run as microservices communicating via a network using a flow-based approach.

The element typically comprises a section-based format having at least the following functional section blocks: imports; parameters; data; physical inputs; requirements; setup; and execution steps. Optionally, the element may further comprise at least one additional section that relates to physical outputs, analysis and/or validation.

The Import section block suitably defines a name for the element, and specifies what additional protocols, parts or unit operations are needed to execute the element.

The Parameters section block suitably defines the information inputs to the element. Data types can be any of the built-in types from high level programming languages such as Google® Go language or Antha™, including int, string, byte, float, as well as specified metric units required in the protocol. Default parameters may be included in this section block.

The Data section block suitably defines the information outputs from the element. The Data section follows the same format as the Parameters block, although typically no default values are given.

The Inputs block suitably defines the physical inputs to the protocol, along with their appropriate type. Physical inputs may comprise starting materials or parts used in the unit operation.

The Outputs section block is optional and may only be present in a unit operation in which a physical product is generated. Examples of protocols that output a physical sample may, thus, include a new liquid solution containing DNA, enzymes, or cells; a lyophilised preparation comprising biological material; or a frozen sample comprising a biopolymer.

The Requirements block is typically executed by a protocol before it begins work, to allow confirmation that the states of any inputs are suitable for successful completion of the unit operation.

The Setup section block is performed once the first time that an element is executed. This can be used to perform any configuration that is needed globally for the element, and is also used to define any special setup that may be needed for groups of concurrent tasks that might be executed at the same time. Any variables that need to be accessed by the steps function globally can be defined here as well.

The functional core of the element of the invention is defined within the Steps section block. The Steps block describes the actual steps taken to transform a set of input parameters and samples into the output data and samples. The Steps are a kernel function, meaning they share no information for every concurrent sample that is processed, and define the workflow to transform a single block of inputs and samples into a single set of outputs.

The Analysis section block is optional and defines how the results of the Steps block should be transformed into final values, if appropriate.

The Validation section block is optional and allows the definition of specific tests to verify the correct execution of an element, along with reporting capabilities as well as the ability to declare the execution a failure.

The placement order of the section blocks within the element may be varied in alternative embodiments of the invention. In addition, section blocks may be combined to give dual functionality and additional section blocks may be added to expand functionality beyond the element set out in FIG. 3.

The invention is further illustrated by the following non-limiting example.

EXAMPLE

In this example, a unit operation of a biological process is defined within the high level biology language Antha™. The element defines a Bradford assay, which is a molecular biology assay used to quantify the amount of protein in a physical sample.

Syntax wise, Antha™ is an extension of the Go language (www.golang.org), and shares a focus on describing concurrent processes functionally. Any execution of a workflow is intended to describe a large array of parallel processes, and is described from the standpoint of the smallest appropriate unit of operation. In the case of this Element, that is the set of actions to process a single physical sample, even though this protocol will normally be run on arrays of samples at the same time. A core purpose of the Antha™ system is to establish a de facto standard language for defining protocols and parts for use in biological experimentation. Therefore, it is designed to mask some of the programming detail from the user and focus on the biology.

Imports:

```
protocol bradford
import (
    "plate_reader"
    "github.com/sajari/regression"
    "standard_labware"
)
```

The Antha™ Element starts by defining a name for the protocol, in this case bradford, and listing what additional protocols or Go libraries are needed to execute the bradford protocol. The Antha™ compiler is intelligent enough to identify whether the imports are existing Go libraries, or other Antha™ Elements, and can be transparently imported directly from source code repositories such as Github (www.github.com).

Parameters:

```
// Input parameters for this protocol (data)
Parameters {
    var SampleVolume Volume = 15.(uL)
    var BradfordVolume Volume = 5.(uL)
    var Wavelength Wavelength = 595.(nm)
    var ControlCurvePoints uint32 = 7
    var ControlCurveDilutionFactor uint32 = 2
    var ReplicateCount uint32 = 1 // Note: 1 replicate means experiment is in duplicate, etc.
}
```

The Parameters block defines the information inputs to the Bradford Element. Data types can be any of the built-in types from the Go language, such as int, string, byte, float, as well as the strongly typed scientific types introduced by the Antha™ language, such as the metric units. Parameter declarations follow the syntax of var VariableName VariableType=OptionalDefaultValue.(OptionalUnit)

For Example:

go var ExampleVolume Volume=15.(uL)

means "Create a parameter named ExampleVolume, which only accepts volume units, with a default value of 15 microliters. By convention variables are named in Upper-CamelCase (using an Upper-case letter for each word as a single name). All Parameters are visible to other Elements, so also by convention they start with an Upper-case letter.

ReplicateCount is a special variable, which tells Antha™ to run ReplicateCount additional copies of each sample. The association of the results, and impact on workflow is automatically handled by the system.

ReplicateCount is a special variable, which tells Antha™ to run ReplicateCount additional copies of each sample. The association of the results and impact on workflow is automatically handled by the system.

Data

```
// Data which is returned from this protocol, and data types
Data {
    var SampleAbsorbance Absorbance
    var ProteinConc Concentration
    var RSquared float32
    var control_absorbance [control_curve_points+1]Absorbance
    var control_concentrations [control_curve_points+1]float64
}
```

The Data block defines the information outputs from the Bradford Element. Declaration follows the same format as the Parameters block, although no default values are given. By convention, results which may be consumed as outputs by other Elements are named with an Upper-case first letter. Variables which start with a lower-case first letter are intended for use only within the protocol, and while the values will be logged, they are not available to any other Antha™ Elements. Additionally, they are shared across all executing copies of an Element, which requires their use to be carefully considered to avoid concurrency problems.

Inputs:

```
// Physical Inputs to this protocol with types
Inputs {
    var Sample WaterSolution
    var BradfordReagent WaterSolution
    var ControlProtein WaterSolution
    var DistilledWater WaterSolution
}
```

The Inputs block defines the physical inputs to the protocol, along with their appropriate type. For example, in this block, all the types are WaterSolutions, meaning they can be operated on by a standard liquid handling robot, or manual pipette operations. Additional attributes of the physical samples are used by the Antha™ Execution system to plan the optimal way to perform physical actions such as mixing on samples based on their types.

Declaration syntax follows the form of the information variables, with the exceptions that no default value is declared.

Outputs:

```
// Physical outputs from this protocol with types
Outputs {
// None
}
```

This protocol is a destructive protocol, meaning that all of the intermediates and the final sample created as a result of this assay needs to be destroyed after performing the protocol. However, many protocols also output a physical sample, such as a new liquid solution containing DNA, enzymes, or cells. By default, any physical sample which is not passed to an Output is scheduled for destruction, with methods appropriate to the safety level of the sample (such as having to autoclave genetic materials, etc).

Requirements:

```
Requirements {
// None
}
```

The Requirements block is executed by a protocol before it begins work, to allow confirming the state of any inputs. For example, a test like require (!Sample.Expired( )) would explicitly confirm that the input sample had not, for the information on the type of sample available to the Antha™ system, expired by being left outside of a temperature controlled environment for too long. By default, Antha™ confirms items such as whether samples have expired automatically, and this block is provided primarily as a convenience for certain classes of more complex tests needed to validate complex inputs such as DNA assembly protocols.

Setup:

```
Setup {
control.Config(config.per_plate)
var control_curve[ControlCurvePoints + 1]WaterSolution
for i:= 0; i < control_curve_points; i++ {
    go func(i) {
        if (i == control_curve_points) {
            control_curve[i] =
mix(distilled_water(sample_volume) +
bradford_reagent(bradford_volume))
        } else {
            control_curve[i] =
serial_dilute(control_protein(sample_volume), control_curve_points,
control_curve_dilution_factor, i)
        }
        control_absorbance[i] =
plate_reader.read(control_curve[i], wavelength)
    }
}
}
```

The Setup block is performed once the first time that an Element is executed. This can be used to perform any configuration that is needed globally for the Element, and is also used to define any special setup that may be needed for groups of concurrent tasks that might be executed at the same time. Any variables that need to be accessed by the Steps function globally can be defined here as well, but need to be handled with care to avoid concurrency problems.

In the context of this Bradford Element, the Control library is used to enable the protocol to define a block of samples that need to be performed in concert with any block of tasks. For example, each 96 well plate of samples needs to have a set of control samples added to it to enable the calculation of the amount of protein in each sample. Creating these control samples is done via a serial dilution of a known protein sample, using up to ControlCurvePoints+1 samples in each block.

Steps:

```
Steps {
var product = mix(Sample(SampleVolume) +
BradfordReagent(BradfordVolume))
SampleAbsorbance = PlateReader.ReadAbsorbance(product, Wavelength)
}
```

The Steps block defines the actual steps taken to transform a set of input parameters and samples into the output data and samples. The Steps are a kernel function, meaning they share no information for every concurrent sample that is processed, and define the workflow to transform a single block of inputs and samples into a single set of outputs, even if the Element is operating on an entire array (such as micro-titre plate of samples at once).

In this Bradford Element, a new sample is created, which is the result of mixing SampleVolume amount of the physical input, Sample. Note: no physical locations, layouts, or methods are required, as the Antha™ Execution layer manages determining the capabilities to perform library functions such as the mix function depending on the equipment registered with the system. Where automated methods of sample transport or liquid handling are not available, it falls back to providing manual instructions.

The newly created sample, product, is then passed to another Antha™ Element, which in this case represents a device driver for a plate reader, to perform a measurement on the sample. Where such processing needs to be batched (such as performing it a plate at a time) the system automatically manages the scheduling of samples to be collocated on a shared micro-titre plate.

Lastly, the results of the plate reader are stored as the output data variable SampleAbsorbance.

Analysis:

```
Analysis {
// need the control samples to be completed before doing the analysis
control.WaitForCompletion( )
// Need to compute the linear curve y = m * x + c
var r regression.Regression
r.SetObservedName("Absorbance")
r.SetVarName(0, "Concentration")
r.AddDataPoint(regression.DataPoint{Observed :
ControlCurvePoints+1, Variables : ControlAbsorbance})
r.AddDataPoint(regression.DataPoint{Observed :
ControlCurvePoints+1, Variables : ControlConcentrations})
r.RunLinearRegression( )
m := r.GetRegCoeff(0)
c := r.GetRegCoeff(1)
RSquared = r.Rsquared
ProteinConc = (sample_absorbance − c) / m
}
```

The Analysis block defines how the results of the Steps can be transformed into final values, if appropriate. Computing the final protein concentration of a Bradford assay requires having the data back from the control samples, performing a linear regression, and then using those results to normalize the plate reader results.

To start, the control .WaitForCompletion( ) is a utility method saying that the Analysis needs to wait for the concurrent control samples to be fully processed before analysis can continue. The actual linear regression is then performed by using an existing Go library for linear regression, which like all Go code, can be seamlessly included in Antha™.

Lastly, the final normalized result (the protein concentration in the sample) is stored in the ProteinConc variable where it can be accessed by downstream Elements.

Validation:

```
Validation {
if SampleAbsorbance > 1 {
    panic("Sample likely needs further dilution")
}
if (RSquared < 0.9) {
    warn("Low r_squared on standard curve")
}
if (RSquared < 0.7) {
    panic("Bad r_squared on standard curve")
}
// TODO: add test of replicate variance
}
```

The Validation block allows the definition of specific tests to verify the correct execution of an Element, along with reporting capabilities (and the ability to declare the execution a failure). For example, the Bradford assay can only handle a specific linear range of concentrations, so if the amount of protein in the sample is above or below that range, the assay will fail.

The solution in such a case is to rerun the assay, with a different dilution factor, however as the Bradford Element is a destructive assay, it may require the generation of more source material which may not be possible, preventing the Element alone from handling such an error.

Validation checks can be grouped as destructive or non destructive. All the tests performed in this example are non-destructive, as they simply analyse the data. However, in other types of Elements, a validation test may require the consumption of some of a sample, such as to run a mass spec trace, and as such only random dipstick testing may be required rather than validating every sample which is executed. Policies such as dipstick validation testing can be configured in the Antha™ Execution environment.

Unless otherwise indicated, the practice of the present invention employs conventional techniques of chemistry, computer science, statistics, molecular biology, microbiology, recombinant DNA technology, and chemical methods, which are within the capabilities of a person of ordinary skill in the art. Such techniques are also explained in the literature, for example, T. Cormen, C. Leiserson, R. Rivest, 2009, Introduction to Algorithms, $3^{rd}$ Edition, The MIT Press, Cambridge, Mass.; L. Eriksson, E. Johansson, N. Kettaneh-Wold, J. Trygg, C. Wikstom, S. Wold, Multi- and Megavariate Data Analysis, Part 1, $2^{nd}$ Edition, 2006, UMetrics, UMetrics AB, Sweden; M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

The invention claimed is:

1. A computer-implemented method for performing a biological process that includes a step involving one or more of a reproducible and scalable transformation of a material into a physical product or a quantification of an amount of a molecule in the material, the method comprising:
   implementing at least one unit operation according to a standardized element structure of a combination of elements that are each reproducible and scalable in a plurality of workflows including a workflow to perform the biological process, wherein the unit operation is a self-contained process of the biological process and the element structure includes a plurality of functional section blocks including at least one selected from the group consisting of imports, parameters, data, physical inputs, requirements, setup, and execution steps; and
   controlling a physical element to implement the at least one unit operation of the biological process to perform the reproducible and scalable transformation of the material into the physical product.

2. The method of claim 1, wherein the element structure further comprises at least one additional section block selected from the group consisting of: physical outputs, analysis and validation steps.

3. The method of claim 1 wherein the element structure comprises at least the sections blocks defining: imports; parameters; data; physical inputs; requirements; setup; and execution steps.

4. The method of claim 1, wherein the biological process comprises at least two unit operations, wherein each unit operation is defined according to a standardized element structure.

5. The method of claim 4, wherein the at least two unit operations are non-identical.

6. The method of claim 1, wherein the unit operation is selected from the group consisting of: a conversion; a reaction; a purification; a construct assembly step; an assay or analysis such as a quantification of a product, a by-product or reagent; a nucleotide or protein/peptide synthesis; a cell culture; an incubation; a restriction; a ligation; a mutation; an inoculation; a lysis; a transformation; an extraction; the conditioning of a product; and an amplification.

7. The method of claim 1, wherein the biological process is a manufacturing process.

8. The method of claim 1, wherein the biological process is an analytical process.

9. A non-transitory computer readable medium storing computer-readable instructions for performing a biological process that includes a step involving one or more of a reproducible and scalable transformation of a material into a physical product or a quantification of an amount of a molecule in the material, the instructions comprising:
   instructions for implementing a plurality of unit operations, each unit operation being suitable for use within a biological process and is defined according to a standardized element structure of a combination of elements that are each reproducible and scalable in a plurality of workflows including a workflow to perform a biological process, wherein each unit operation is a self-contained process of a biological process and the element structure includes a plurality of functional section blocks including at least one selected from the group consisting of imports, parameters, data, physical inputs, requirements, setup, and execution steps; and
   instructions for controlling a physical element to implement at least one of the plurality of unit operations of a biological process to perform the reproducible and scalable transformation of the material into the physical product or the quantification of the amount of the molecule in the material.

10. The non-transitory computer readable medium of claim 9, wherein the element structure further comprises at least one additional section block selected from the group consisting of: physical outputs, analysis and validation steps.

11. The non-transitory computer readable medium of claim 9, wherein the element structure comprises at least the section blocks defining: imports; parameters; data; physical inputs; requirements; setup; and execution steps.

12. An apparatus comprising the non-transitory computer readable medium of any of claim 9.

13. A computer-implemented method for designing an experiment comprising the steps of:
   (i) selecting an input and a desired output for the experiment, wherein the input comprises physical input and the output is selected from either or both of a physical output and an information output; and
   (ii) determining a reproducible and scalable process for conversion of the input to the desired output, wherein the reproducible and scalable process comprises at least one unit operation, and wherein the unit operation is selected from a database that comprises a plurality of potential unit operations;
   wherein the unit operation is defined according to a standardized element structure of a combination of elements that are each reproducible and scalable in a plurality of workflows including a workflow to perform the biological process, wherein the unit operation is a self-contained process of the biological process and the element structure includes a plurality of functional section blocks including at least one selected from the group consisting of imports, parameters, data, physical inputs, requirements, setup, and execution steps; and
   (iii) controlling a physical element to implement the at least one unit operation of the biological process to perform the reproducible and scalable transformation of the material into the physical product.

* * * * *